United States Patent [19]

Capetola et al.

[11] 4,243,673

[45] Jan. 6, 1981

[54] ANALGESIC COMPOSITIONS AND METHODS OF USE

[75] Inventors: Robert J. Capetola, Doylestown, Pa.; John L. McGuire, White House Station, N.J.

[73] Assignee: Ortho Pharmaceutical Corporation, Raritan, N.J.

[21] Appl. No.: 971,472

[22] Filed: Dec. 20, 1978

[51] Int. Cl.$^2$ .................. A61K 31/38; A61K 31/165
[52] U.S. Cl. ..................................... 424/275; 424/324
[58] Field of Search ............................... 424/275, 324

[56] References Cited

PUBLICATIONS

Merck Index, 7th Ed. (1960), pp. 537–538
Chem. Abst., 84-38939k (1976)
Chem. Abst., 84-43737x (1976).

*Primary Examiner*—Stanley J. Friedman
*Attorney, Agent, or Firm*—Benjamin F. Lambert

[57] ABSTRACT

An analgesic composition comprising a mixture of a non-narcotic analgesic compound and L-methyl-4-[2-thienylcarbonyl] benzene acetic acid is described. Potentiation of the analgesic effect is observed in the combination.

5 Claims, 2 Drawing Figures

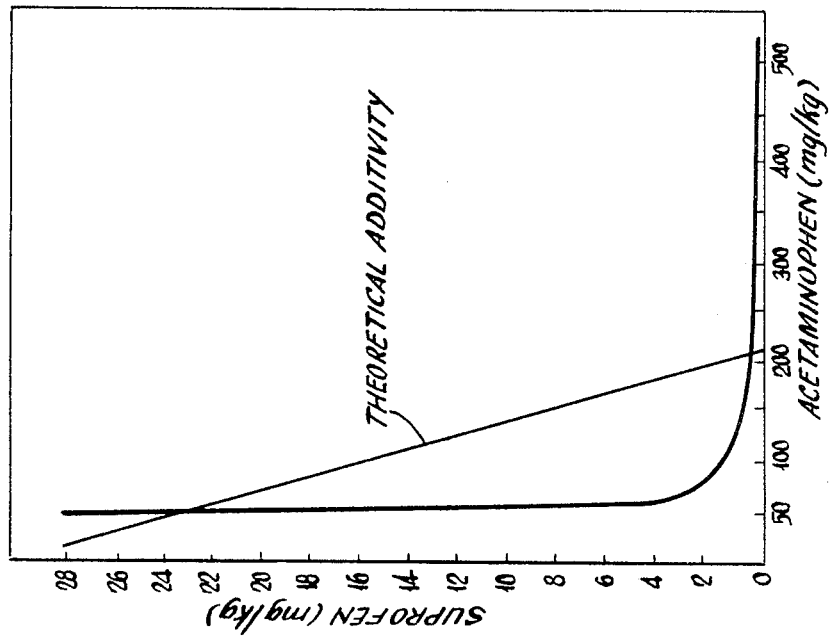
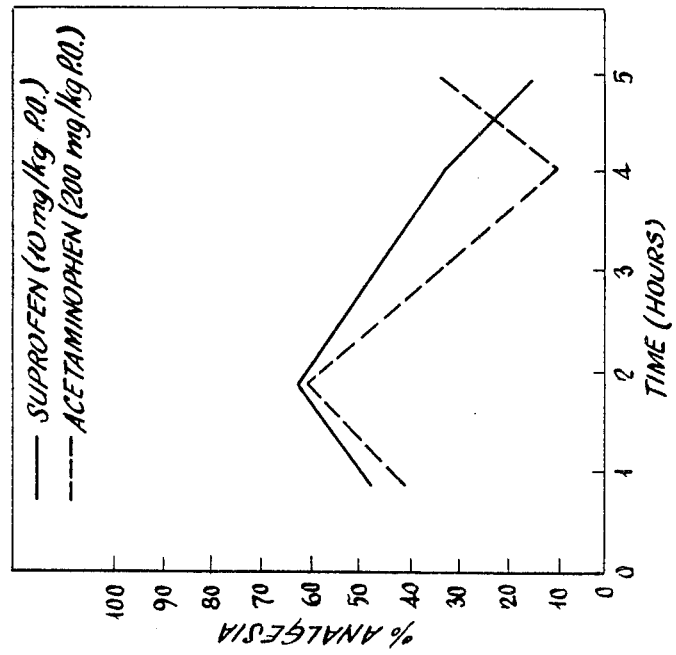

ANALGESIC COMPOSITIONS AND METHODS OF USE

This invention relates to a method of potentiating the effect of certain analgesics by the addition of α-methyl-4-(2-thienylcarbonyl) benzene acetic acid.

The most commonly employed method of managing pain involves the systemic administration of analgesics. Analgesics by definition include drugs which through their action on the nervous system reduce or abolish suffering from pain without producing unconsciousness. This result may be brought about in several ways: (i) by interfering with conduction of noxious impulses or abnormal motor responses by direct action on the peripheral nerves or the brain; (2) by changing the attitude or mood of the patient toward pain, by promoting freedom from anxiety, mild euphoria, or a feeling of well-being or by inducing apathy to the painful experience; (3) by producing sedative and soporific effects; (4) by affecting peripheral modulators of pain; and (5) by producing a combination of two or more of these effects.

Close analysis reveals that analgesics comprise several heterogeneous groups of drugs which act on various parts of the physiopsychologic system concerned with pain. These include those which have their effect primarily on the central nervous system, for example, the opiates and those which exert a local action on the pain conduction system, such as salicylates, for example. The analgesics to which the present invention relates are those which affect primarily the peripheral rather than the central nervous system.

In selecting the type of analgesic to be employed, the quality and intensity of pain are the most important considerations. Mild pain can be adequately controlled with non-addictive analgesics. Opiates and opioids should be postponed until the weaker drugs prove ineffective. It is often desirous to administer a combination of drugs which produces the same result by entirely different mechanisms.

The drugs which comprise the group known as non-addictive analgesics include among others the salicylates, para-aminophenols and pyrazolons. Derivatives of salicylic acid which are of value in pain control consist of salts or esters of salicylic acid and salicylate esters of organic acids. Examples of such derivatives include sodium salicylate, methyl salicylate, salicylsalicylic acid, acetylsalicylic acid (aspirin), salicylamide (Salamide, Salicum, Saldrin, Liquiprin) and phenetsal (Salophen). Examples of para-amino-phenols include acetanilid (Antifebrin), and acetophenetidin (phenacetin) acetaminophen (Apamide, Tempra). Examples of pyrazolons having analgesic activity include antipyrene (phenazone), aminopyrine (Pyramidon), phenylbutazone (Butazolidin) and dipyrene (Novaldin). The non-addictive analgesics have a significant advantage in that they do not produce tolerance or addiction.

It may be generally stated that one should always seek and use the minimal effective dose of any drug. This requires the exercise of good clinical judgment, particularly when dealing with pain which is the most subjective of all symptoms.

In very large doses the non-narcotic analgesics may cause a variety of side effects including headache, dizziness, dimness of vision, nausea, increased respiratory or pulse rates and, in some cases, painless bleeding from the gastrointestinal tract. Recovery is usually prompt, however, if the drug is withdrawn.

There is a serious need, therefore, for more potent non-addictive systemic analgesic drugs which can produce interruption of pain by the administration of small doses of the drug. One way of achieving this result would be to enhance the analgesic effectiveness of a known analgesic by the addition of a second compound which will potentiate the pain controlling property of the drug without causing any additional side effects. By potentiating the analgesic effect it is possible to use smaller amounts of each drug in combination and thereby reduce the side effects attendant to a given drug.

One of the objects of the present invention is to provide a method of potentiating the analgesic effect of compounds having known analgesic activity.

Another object of this invention is to provide an analgesic composition comprising one or more known analgesics in combination with a compound which potentiates the analgesic effect.

Another object of this invention is to provide a method of controlling pain by the administration of a composition comprising one or more analgesics and a compound which potentiates the analgesic activity.

These and other objects of the invention will become apparent from the following detailed description.

α-Methyl-4-(2-thienylcarbonyl) benzene acetic acid (suprofen) is a new, orally effective, non-narcotic analgesic which has been shown to be more potent than D-propoxyphene and aspirin. It has been found, however, that the addition of suprofen to non-addictive analgesics, such as, for example, acetaminophen, causes a potentiation of the analgesic activity. Since both compounds are analgesics one would expect the effectiveness of a combination of the two compounds to be merely additive. However, tests have shown that the effectiveness of the combination is not merely the sum of the activity of the components; the combination results in a new analgesic composition which is more effective in controlling pain than would be expected from the cumulative effect of a combination of the two active ingredients.

The compositions of the present invention consist of a combination of suprofen and a non-narcotic analgesic in an intimate admixture with a pharmaceutically acceptable carrier according to conventional pharmaceutical techniques. One or more non-addictive analgesics may be combined with suprofen in forming the composition. The carrier may take a wide variety of forms depending upon the form of preparation desired for administration i.e. oral or parenteral. In preparing the compositions in oral dosage form any of the usual pharmaceutical media may be employed such as, for example, water, glycols, oils, alcohols, flavoring agents, preservative coloring agents and the like in the case of oral liquid preparations such as, for example, suspensions, elixirs and solutions. Carriers such as starches, sugars, diluents, granulating agents, lubricants, binders, disintegrating agents and the like may be employed in the case of solid oral preparations such as, for example, powders, capsules and tablets. Because of their ease in administration, tablets and capsules represent the most advantageous oral dosage unit form. If desired, the tablets may be sugar coated or enteric coated by standard techniques. For parenterals, the carrier will usually comprise sterile water, although other ingredients may be added to aid solubility or for preservative purposes.

Injectable suspensions may also be prepared, in which case appropriate liquid carriers, suspending agents and the like may be employed.

The compositions of the present invention will generally contain in addition to the analgesic per dosage unit, i.e. tablet, capsule, powder etc., from about 25 to 400 mg. of suprofen, and preferably from about 50 to 200 mg. The other analgesic ingredient (or ingredients) is generally present in preferred doses ranging from about 0.1 g. to about 0.6 gm, although doses as large as 50 to 800 mg. may be employed.

The analgesic activity of suprofen and in combination with one or more non-addictive analgesics is determined by means of the rat adjuvant arthritic flexion test. The model employed is unique in that it represents pathologically induced pain. Experiments are designed to assess the interaction activity of the combination. In a randomized study ED50 values of the non-addictive analgesic alone and in combination with five doses of suprofen are plotted as isobolograms. Potentiation is indicated by the fact that most of the points fall below the line of additivity.

MATERIALS AND METHODS

Polyarthritis is induced in male Lewis strain rats by the injection (0.1 ml) of a suspension of Mycobacterium butyricum (0.75 mg) in Freund's incomplete adjuvant into the subplantar tissue of the left hindpaw on Day 0. Seventeen days later the rats are tested for their tendency to vocalize following flexion of the tarso-tibial joint of the non-injected paw (Kuzuna, S. and Kiyohisa, K., Chem. Pharm. Bull. 23:1184-1191, 1975). For acceptance into the test group, a rat must vocalize five successive times following five gentle flexions of the joint.

The following day the drug or drug combinations are administered orally and the number of vocalizations is recorded after five flexions a 1, 2, 3, 4 and 5 hours. The data presented include only the two hour data as this is the time of peak activity (FIG. 1). Compounds are suspended in 0.5% methocel and administered at 5 ml/kg of the appropriate dose. For the combination doses, both suprofen and the companion compound are suspended in the same vial.

A total of thirty groups (8-10 rats/group) were employed for the entire experiment. Randomization of treatment was done by assigning each cage a number drawn from a box. The experiment was carried out in a single-blind manner. The study was designed so that each dose-response curve for the companion compound (30, 60, 120 and 240 mpk) was repeated in the presence of a different concentration of suprofen (0.3, 1.0, 3.0, 10.0 and 30.0 mpk). ED50 values were calculated for each dose-response curve interaction. The criteria used for an effect are such that if an animal squeaked three times or more it was considered non-analgesic, two times or less analgesic. The ED50 values were extrapolated to the X-axis and these concentrations of acetaminophen were plotted against the five doses of suprofen, thus yielding isobolographs. The statistical analysis performed is based on the method of Scaf, A.H.J. (Arch. Int. Pharmacodyn, 208, 138-165, 1974).

RESULTS AND DISCUSSIONS

Analgesic activity of acetaminophen and suprofen was evaluated in 266 adjuvant arthritic rats (8-10 rats/group) using inhibition of the squeak response as the index of activity.

Both suprofen and acetaminophen are effective analgesics in this test. The results of the test are shown in Table 1.

TABLE 1.

ED50 Values for Acetaminophen or a Combination of Acetaminophen and Suprofen

| Drug or Combination | # Animals | ED50 (mg/kg) |
|---|---|---|
| Acetaminophen | 39 | 535.8 |
| Acetaminophen + Suprofen 0.3 mg/kg | 36 | 195.9 |
| Acetaminophen + Suprofen 1.0 mg/kg | 39 | 118.0 |
| Acetaminophen + Suprofen 3.0 mg/kg | 37 | 65.2 |
| Acetaminophen + Suprofen 10.0 mg/kg | 37 | 75.9 |
| Acetaminophen + Suprofen 30.0 mg/kg | 38 | 62.2 |

The ED50 for acetaminophen alone is 535.8 mg/kg and for suprofen alone the ED50 is approximately 30 mg/kg. However, as Table 1 indicates, with progressively higher doses of suprofen, the ED50 value for acetaminophen progressively decreases, and then flattens out at the 3 mg/kg dose level. In order to determine whether this represents additivity or potentiation, the responses were graphed using the ED50 values and doses of suprofen as rectangular coordinates and an isobologram was plotted (FIG. 2) with acetaminophen along the X-axis and suprofen values along the Y-axis. Most of the points lie below the theoretical straight line joining the two points with the coordinates. The straight line is defined as the line of additivity, the hyperbola as the line of potentiation. A statistical analysis was performed and the line was determined to be significantly different from linearity ($p < 0.01$).

The plot of the experimental points (FIG. 3) yielded an hyperbola which was determined to be statistically different from linearity ($P < 0.01$). The experimental data represent the lower limit fiducial interval of the acetaminophen $ED_{50}$ values as a function of the suprofen dosage. The data indicate that suprofen potentiates the analgesic activity of acetaminophen.

What is claimed is:

1. A method of controlling pain in mammals which comprises administering to a mammal an effective amount of a composition comprising from about 0.5 mg/kg to about 22 mg/kg of α-methyl-4-(2-thienylcarbonyl) benzene acetic acid and from about 1 mg/kg to about 200 mg/kg of N-(4-hydroxyphenyl) acetamide.

2. The method of claim 1 wherein the N-(4-hydroxyphenyl) acetamide is present in about 1 mg/kg to 16 mg/kg and the α-methyl-4-(2-thienylcarbonyl) benzene acetic acid is present in from about 1 mg/kg to about 12 mg/kg.

3. A composition useful in controlling pain in mammals comprising in combination from about 1 mg/kg to about 200 mg/kg of N-(4-hydroxyphenyl) acetamide, from about 0.5 mg/kg to about 22 mg/kg of α-methyl-4-(2-thienylcarbonyl) benzene acetic acid and a pharmaceutically acceptable carrier.

4. The composition of claim 3 wherein the N-(4-hydroxyphenyl) acetamide is present in an amount from about 1.0 mg/kg to 16 mg/kg.

5. The composition of claim 3 wherein α-methyl-4-(2-thienylcarbonyl) benzene acetic acid is present in an amount from about 1.0 mg/kg to about 12 mg/kg.

* * * * *

UNITED STATES PATENT AND TRADEMARK OFFICE
CERTIFICATE OF CORRECTION

PATENT NO. : 4,243,673
DATED : January 6, 1981
INVENTOR(S) : Robert J. Capetola and John L. McGuire It is certified that error appears in the above-identified patent and that said Letters Patent are hereby corrected as shown below:

Column 4, Table 1, Line 15, "10.0 mg/kg" appears in wrong column in the table, should follow Suprofen in the column in the table headed "Drug or Combination"

Signed and Sealed this

Thirteenth Day of October 1981

[SEAL]

Attest:

GERALD J. MOSSINGHOFF

Attesting Officer     Commissioner of Patents and Trademarks